United States Patent
Talton

(10) Patent No.: US 11,202,788 B2
(45) Date of Patent: Dec. 21, 2021

(54) TOPICAL DOXYCYCLINE HYDROGEL WITH IMPROVED LONG-TERM STABILITY

(71) Applicant: Nanopharmaceutics, Inc., Alachua, FL (US)

(72) Inventor: James Talton, Alachua, FL (US)

(73) Assignee: Nanopharmaceutics, Inc., Alachua, FL (US)

( * ) Notice: Subject to any disclaimer, the term of this patent is extended or adjusted under 35 U.S.C. 154(b) by 95 days.

(21) Appl. No.: 16/547,658

(22) Filed: Aug. 22, 2019

(65) Prior Publication Data

US 2021/0052607 A1 Feb. 25, 2021

(51) Int. Cl.
| | |
|---|---|
| *A61K 31/65* | (2006.01) |
| *A61P 17/00* | (2006.01) |
| *A61K 9/00* | (2006.01) |
| *A61K 9/06* | (2006.01) |
| *A61K 47/10* | (2017.01) |
| *A61K 47/12* | (2006.01) |
| *A61K 47/38* | (2006.01) |

(52) U.S. Cl.
CPC ............ *A61K 31/65* (2013.01); *A61K 9/0014* (2013.01); *A61K 9/06* (2013.01); *A61K 47/10* (2013.01); *A61K 47/12* (2013.01); *A61K 47/38* (2013.01); *A61P 17/00* (2018.01)

(58) Field of Classification Search
None
See application file for complete search history.

(56) References Cited

U.S. PATENT DOCUMENTS

| | | | |
|---|---|---|---|
| 2,903,395 | A | 9/1959 | Saliver |
| 5,238,684 | A | 8/1993 | Fregly et al. |
| 8,828,363 | B2 | 9/2014 | Eirew |
| 2004/0151743 | A1 | 8/2004 | Nomura et al. |
| 2005/0175707 | A1 | 8/2005 | Talton |
| 2008/0188445 | A1 | 8/2008 | Chilcott |
| 2009/0136514 | A1 | 5/2009 | Power |
| 2010/0129448 | A1* | 5/2010 | Talton .................. A61K 9/0014 424/484 |
| 2012/0028929 | A1* | 2/2012 | Power .................. A61K 9/0048 514/153 |
| 2012/0277199 | A1* | 11/2012 | Ye ........................... A61P 31/04 514/171 |
| 2014/0147504 | A1 | 5/2014 | Salman et al. |

FOREIGN PATENT DOCUMENTS

| | | |
|---|---|---|
| EP | 1902706 B1 | 11/2016 |
| WO | 0119362 | 3/2001 |
| WO | 2009072007 A3 | 6/2009 |
| WO | 2018234865 A1 | 12/2018 |

OTHER PUBLICATIONS

Wikipedia (https://en.wikipedia.org/wiki/Autoclave (downloaded on May 7, 2020)) (Year: 2020).*
K. Eger, "4-Epidoxycycline: an alternative to doxycycline to control gene expression in conditional mouse models", Biochemical and Biophysical Research Communications 323 (2004) 979-986.
Joseph B. Bogardus et al., "Solubility of Doxycycline in Aqueous Solution", Journal of Pharmaceutical Sciences, vol. 68, No. 2, Feb. 1979.
Remington Essentials of Pharmaceutics, Ed. Linda Felton, PhD, Published by Pharmaceutical Press (2012).
PCT Notification of Transmittal of ISA & Written Opinion of the International Searching Authority, or the Declaration.

* cited by examiner

*Primary Examiner* — Jake M Vu
(74) *Attorney, Agent, or Firm* — McGurk Group LLC

(57) ABSTRACT

The present invention relates to an aqueous hydrogel composition for topical application to skin or a wound, comprising doxycycline with carboxy-methyl-cellulose, glycerol, citric acid, and at least one pH stabilizer, wherein the composition includes a suspension or dispersion of particles of doxycycline chelated with calcium, said particles have an average diameter less than or equal to about 100 microns, wherein the doxycycline chelated with calcium is present in an amount ranging from greater than about 0.1 weight % to about 3 weight %, wherein the composition includes less than 0.5 weight % 4-epidoxycycline. The present invention also describes methods for making a composition for topical applications as well as methods of treating skin or a wound with an aqueous hydrogel composition comprising doxycycline with carboxy-methyl-cellulose, glycerol, citric acid, and at least one pH stabilizer.

1 Claim, No Drawings

TOPICAL DOXYCYCLINE HYDROGEL WITH IMPROVED LONG-TERM STABILITY

BACKGROUND

Wound dressings must be designed with care so the application does not increase insult or inflammation. One of the major determinants of wound healing involves keeping the wound wet, since dry dressings retard healing. The thickness, diffusivity, occlusiveness, and osmotic pressure of a wound dressing are responsible for the direction and rate of movement of gases and water across the membrane. The allocation of water between a wound, blood plasma, and cells depends upon the relative osmotic pressures between these sites. Besides electrolytes, glycerol and other compounds may be used to improve wound remodeling and energy metabolism, including glucose, pyruvate, alanine, and/or lactate, which are particularly useful because they function to enhance the energy available for cells (U.S. Pat. No. 5,238,684), as well as arginine for wound healing.

In some cases, it is of interest to incorporate tetracycline, or its derivatives, in an aqueous solution at a higher concentration then the solubility of the drug permits, requiring a uniform dispersion of particles. Doxycycline monohydrate, for example, is very slightly soluble in water having an aqueous solubility of less then 0.8 mg/ml at pHs above 6 (Bogardus, J B, et al. 1979. J. Pharm Sci 68:188-94). Incorporation of higher concentrations, 1% by mass for example, without homogenization or vigorous mixing, leads to a gritty suspension not applicable to wounds. The size of the drug particle in the suspension, as well as the viscosity and agglomeration properties of the particles in the mixture, may be manipulated by changing the mixing conditions and temperatures during manufacturing. In such cases, fine particle suspensions, for example, are desirable to provide a homogenous dispersion throughout the matrix and prevent grittiness. A particle suspension allows for more drug to be available in the hydrogel above the solubility limit at a given pH. Unfortunately, doxycycline in an aqueous solution will degrade into epimers or oxidative degradation products, thus decreasing the shelf life of the compound. Doxycycline degrades into 4-epidoxycycline and 6-epidoxycycline and other degradation products when in solution. In particular, 4-epidoxycycline (CAS Number 6543-77-7) is the 4-epimer hepatic metabolite of the antibiotic doxycycline and lacks antibiotic activity shown to induce intestinal inflammation in mice (Eger et. al., Biochemical and Biophysical Research Communications 323(3):979-86). Doxycycline drug molecules incorporated as particles in a homogenous suspension are less available for degradation to 4-epidoxycycline.

The dissolution of a drug from suspended particles in a polydisperse suspension was developed by Noyes & Whitney and was later modified by Nernst as $dQ/dt = DA(C_s - C_b)/h$, where $dQ/dt$=Dissolution rate, h=Diffusion layer thickness, Cs=solubility, and Cb=bulk area of particle. This model represents the rapid equilibrium at the solid-liquid interface that produces a saturated solution which diffuses into the bulk solution across a thin diffusion layer. The dissolution rate of the suspension is affected by the particle size (small particles increase the surface area and subsequent dissolution rate) and viscosity. The intrinsic viscosity of a medium affects the dissolution rate of particles because of the diffusion effect. The total viscosity of the dispersion is the summation of the intrinsic viscosity of the dispersion medium and interaction of the particles of the disperse phase as per Stokes-Einstein equation. On enhancement of viscosity the diffusion coefficient decreases, which gives rise to a proportionate decrease in rate of dissolution.

In US 20100129448 by the Inventor, Example 1, the preparation of a "Doxycycline Monohydrate Hydrogel Particulate Delivery System" is described. Previous attempts before 2017 to produce a stable doxycycline-calcium chelate particle suspension were performed adding doxycycline to autoclaved carboxy-methyl-cellulose (CMC) hydrogel at increased temperatures above 90 degrees Celsius to promote a homogenous dispersion while mixing. Calcium chloride and stabilizers (TEA, citric acid) were added to the CMC hydrogel, whereby calcium was available to chelate the Doxycycline as the hydrogel cooled under mixing. The resulting combination was mixed under high shear conditions (paddle mixer and sonication) as described in U.S. Pat. Appl. Pub. No. 2005/0175707 at elevated temperature (40 to 50 degrees Celsius) to generate a homogenous dispersion. The doxycycline hydrogel was then refrigerated followed by filling into medical-grade packets. Using these conditions, the autoclaved CMC allowed for sterilization of the hydrogel but the doxycycline was exposed to elevated temperatures (70 degrees to greater than 90 degrees Celsius) before cooling. The resulting doxycycline hydrogel was typically yellow-brown with less then one year shelf-life (before the doxycycline concentration decreased below 90% of the label claim).

In US 2009/0035229, Eirew teaches an aqueous-based pharmaceutical composition containing a tetracycline antibiotic for use as an oral hygienic treatment, wherein the composition is applied in the oral cavity by swishing (i.e. applied topically to the skin). Eirew teaches the tetracycline-based antibiotic selected from a genus of ten commercially available compounds including oxytetracycline and doxycycline. Eirew teaches a composition comprising doxycycline, the water-soluble calcium salt, calcium chloride; sodium carboxymethylcellulose as a thickener, buffers, as the pH adjustment agent and glycerin as an excipient. Eirew teaches an example in which doxycycline is present in a concentration of 15 mg/ml (i.e. ~1.5% by weight). Further, Eirew teaches said compositions are made by suspending the thickener, sodium carboxymethyl cellulose, in purified water to make a gel. However, Eirew teaches that adding a calcium salt to a dispersion comprising the activated doxycycline gel forms a "solubilized gel". Eirew is silent regarding a composition comprising a dispersion or suspension of particles, wherein the particles comprise a tetracycline chelated with a physiologically acceptable metal salt. Eirew is also silent with respect to the rate of degradation of doxycycline to 4-epidoxycycline, which reduce antimicrobial activity, as well as the conversion of doxycycline to >0.5% 4-epidoxycycline relating to a color change.

In US 2009/0136514 and US 20120028929, Powers teaches an aqueous solution comprising a tetracycline, a chelating agent at a concentration of about 0.1-0.5%, and an antioxidant agent at a concentration of about 0.1-0.5%, wherein the pH of the solution is between about 4.5 and about 7.5. A method for reducing the rate and/or overall extent of degradation of the tetracycline in aqueous solution comprises admixing in a tetracycline containing solution, a chelating agent at a concentration of about 0.1-0.5% and an antioxidant at a concentration of about 0.1-0.5% and, as necessary. Adjusting the pH of the solution so that it is between about 4.5 and about 7.5 is also disclosed. Powers also teaches that doxycycline will degrade into 4-epidoxycycline and 6-epidoxycycline and other degradation products when in solution. The rate of doxycycline epimerization increased with temperature and time. After 12 months of storage at 5 degrees Celsius, 0.025% w/w doxycycline formulation resulted in the appearance 0.0019% w/w 4-epidoxycycline (approximately 10% of starting doxycycline amount). The same storage time at 25 degrees Celsius resulted in the appearance of about 3 times as much 4-epidoxycycline (0.0060 w/w, approximately 20% of starting doxycycline amount). The lack of anti-inflammatory and anti-proteolytic effects of 4-epidoxycycline (as well as 6-epidoxycycline) was demonstrated in a treatment study for an experimental dry eye (EDE) model. Powers is silent with respect to use of a doxycycline suspension to achieve higher doxycycline concentrations as well as the conversion of doxycycline to >0.5% 4-epidoxycycline relating to a color change.

In US 2005/0019396, deVries teaches a process of making a doxycycline calcium complex comprising admixing a solution of calcium chloride with an aqueous solution of doxycycline and adjusting the pH to between 6 and 8 to form a suspension to the doxycycline calcium complex, followed by drying to form a dry granulation (i.e. particles). De Vries teaches forming a solid dosage form by admixing a suspension of the doxycycline calcium complex with one or more pharmaceutically acceptable excipients and treating a bacterial infection by administering said dosage form to a host in need thereof. However, deVries does not teach topical administration of a doxycycline calcium complex and the rate of degradation of doxycycline to 4-epidoxycycline and the conversion of doxycycline to >0.5% 4-epidoxycycline relating to a color change.

In US 2004/0151743, Nomura teaches stable topically administered antibacterial compositions comprises a penem antibiotic. Nomura teaches that in formulating ointments, an active component has to be mixed homogeneously throughout a semisolid base. Nomura teaches that when the active component is in the form of crystals or a crystalline powder it is difficult to achieve homogeneity simply by dispersing the component in a base and therefore requires the component first be ground into fine particles. Nomura teaches to make suitable the crystalline active component for topical administration the preferred particle diameter is 500 microns or less, normally 100 microns or less. Nomura is silent with respect to the rate of degradation of doxycycline in solution to 4-epidoxycycline and 6-epidoxycycline, which reduce antimicrobial activity, as well as the conversion of doxycycline to >0.5% 4-epidoxycycline relating to a color change.

In WO 01/19362, Lawter teaches tetracycline formulations for treating or preventing mucositis, which is applied topically to the oral mucosa. Lawter teaches that tetracyclines in general may not be sufficiently stable in aqueous solutions to permit formulations with long shelf lives at room temperature, i.e. a year or more, to be prepared. Lawter teaches doxycycline as a tetracycline compound used in the disclosed method of treating mucositis. Lawter teaches that polyvalent ion complexes of tetracyclines with magnesium or calcium suspended in water are stable in contact with water at room temperature for two years or more. Further, Lawter teaches aqueous suspensions of tetracycline calcium complexes are stable in contact with water at room temperature for two years or more. Lawter is silent with respect to the rate of degradation of doxycycline in solution to 4-epidoxycycline, which reduces the antimicrobial activity, as well as the conversion of doxycycline to >0.5% 4-epidoxycycline relating to a color change.

In U.S. Pat. No. 2,903,395, Salivar teaches antibiotic compositions comprising a suspension of a salt, calcium dioxytetracycline (a tetracycline antibiotic) which comprises one atom of calcium and two molecules of oxytetracycline. Salivar teaches suspensions containing calcium dioxytetracycline have superior stability compared to aqueous suspensions containing amphoteric dioxytetracycline. Salivar teaches a mastitis formulation, comprising calcium dioxytetracycline that is prepared by passing it through a homogenizer twice at a pressure of 2500 pounds per square inch to provide a homogeneous suspension that, when applied to the udder of a cow (topical administration), brought about rapid and complete alleviation of mastitis. Regarding particle sizes, Salivar teaches that for an oral suspension all solids are reduced to a particle size of less than 100 microns. However, Salivar is silent regarding the size of the particles in the topical (mastitis) formulation. Salivar is also silent with respect to the rate of degradation of doxycycline in solution to 4-epidoxycycline and 6-epidoxycycline as well as the conversion of doxycycline to >0.5% 4-epidoxycycline relating to a color change.

Thus, there remains a need in the art for topical compositions and methods for the delivery of doxycycline, in high concentrations above the aqueous solubility of the compounds, and without the aforementioned problems regarding shelf-life stability. The present disclosure addresses this need by providing, for example, compositions comprising small particles of doxycycline, chelated or otherwise complexed with a physiologically acceptable salt in a physiologically acceptable carrier, such as a hydrogel, with a known rate of degradation to 4-epidoxycycline. It would be an additional benefit if the conversion of doxycycline to >0.5% 4-epidoxycycline resulted in a stability-indicating color change.

SUMMARY OF THE INVENTION

The present invention relates to an aqueous hydrogel composition for topical application to skin or a wound, comprising doxycycline with carboxy-methyl-cellulose, glycerol, citric acid, and at least one pH stabilizer, wherein the composition includes a suspension or dispersion of particles of doxycycline chelated with calcium, said particles have an average diameter less than or equal to about 100 microns, wherein the doxycycline chelated with calcium is present in an amount ranging from greater than about 0.1 weight % to about 3 weight %, wherein the composition includes less than 0.5 weight % 4-epidoxycycline. The present invention also describes methods for making a composition for topical applications as well as methods of treating skin or a wound with an aqueous hydrogel composition comprising doxycycline with carboxy-methyl-cellulose, glycerol, citric acid, and at least one pH stabilizer. The present pharmaceutical composition and associated methods of making the composition, according to the principles of the present invention, overcomes a number of the shortcomings of the prior art by providing a novel aqueous based doxycycline hydrogel composition with improved shelf-life stability (1-2 years or greater) and demonstrates reduced degradation products, including <0.5% 4-epidoxycycline and <1% 6-epidoxycycline, which reduce antimicrobial activity.

DETAILED DESCRIPTON

Disclosed herein are compositions for an aqueous hydrogel composition for topical application to skin or a wound, comprising doxycycline with carboxy-methyl-cellulose, glycerol, citric acid, and at least one pH stabilizer, wherein the composition includes a suspension or dispersion of particles of doxycycline chelated with calcium, said particles have an average diameter less than or equal to about 100 microns, wherein the doxycycline chelated with calcium is present in an amount ranging from greater than about 0.1 weight % to about 3 weight %, wherein the composition includes less than 0.5 weight % 4-epidoxycycline. In one embodiment the composition also includes the formation of 4-epidoxycycline less than 0.5 weight % per year under refrigeration. In another embodiment the storage of the composition for greater than one year under refrigeration, or exposure to higher temperatures, results in the formation of 4-epidoxycycline in amounts greater than 0.5 weight %. In another embodiment the composition is a yellow color when the composition contains an amount of 4-epidoxycycline less than 0.5 weight %. In yet another embodiment the composition is a brown color when the composition contains an amount of 4-epidoxycycline greater than 0.5 weight %. In another embodiment the topical applications include skin and/or a wound.

One non-limiting embodiment of the present disclosure is a method for making a composition for topical applications, comprising doxycycline with carboxy-methyl-cellulose, glycerol, citric acid, and at least one pH stabilizer, a suspension or dispersion of particles of doxycycline chelated with calcium, with the particles having an average diameter less than or equal to about 100 microns, wherein the doxycycline is added in solution at a temperature less than 70 degrees Celsius, wherein the doxycycline chelated with calcium is present in an amount ranging from greater than about 0.1 weight % to about 3 weight %, wherein the composition includes less than 0.5 weight % 4-epidoxycycline, and wherein the composition is refrigerated to slow the production of 4-epidoxycycline. In one embodiment the method includes the formation of 4-epidoxycycline less than 0.5 weight % per year under refrigeration. In another embodiment the method includes the storage of the composition for greater than one year under refrigeration, or exposure to higher temperatures, resulting in the formation of 4-epidoxycycline in amounts greater than 0.5 weight %. In another embodiment the method results in a composition that is a yellow color when the composition contains an amount of 4-epidoxycycline less than 0.5 weight %. In yet another embodiment the method results in a composition that is a brown color when the composition contains an amount of 4-epidoxycycline greater than 0.5 weight %. In another embodiment the method results in a composition where the topical application to the skin and/or a wound.

A non-limiting embodiment disclosed herein is a method of treating skin or a wound with an aqueous hydrogel composition comprising doxycycline with carboxy-methyl-cellulose, glycerol, citric acid, and at least one pH stabilizer, wherein the composition includes a suspension or dispersion of particles of doxycycline chelated with calcium, said particles have an average diameter less than or equal to about 100 microns, wherein the doxycycline chelated with calcium is present in an amount ranging from greater than about 0.1 weight % to about 3 weight %, wherein the composition includes less than 0.5 weight % 4-epidoxycycline, and topically administering the pharmaceutical formulation to skin or a wound on a patient in need thereof.

The present invention relates to topical doxycycline compositions for skin and/or wound application with improved long-term stability and reduced degradation products. Doxycycline in an aqueous hydrogel solution at neutral pH is precipitated with calcium at low temperatures to form a stable doxycycline calcium chelate hydrogel suspension. The composition has improved shelf-life stability and demonstrates reduced degradation products including >0.5 weight % 4-epidoxycycline and <1 weight % 6-epidoxycycline, which reduce antimicrobial activity and can lead to severe hepatotoxicity. A topical doxycycline composition with improved long-term stability and reduced degradation products for ameliorating adverse effects associated with wounds comprising the step of administering topically an effective amount of doxycycline, chelated to calcium in a viscous suspension comprising water, physiologically acceptable salts, and glycerol in a physiologically acceptable carrier system incorporating a natural and/or synthetic polymer, including carboxy-methyl-cellulose.

The present invention relates to topical compositions for skin and/or wound application. A composition to promote wound healing comprising the step of administering topically an effective amount of a tetracycline-class compound, including doxycycline chelated to calcium, in a viscous suspension comprising water, physiologically acceptable salts, and glycerol in a physiologically acceptable carrier system incorporating a natural and/or synthetic polymer, including carboxy-methyl-cellulose. The composition incorporates >0.1 weight % by mass of doxycycline chelated to calcium, as a fine particle suspension of particles less then 100 micrometers measured by optical microscopy.

The compositions may be prepared by heating or autoclaving the hydrogel, then mixing in the tetracycline to disperse and dissolve the compound. Additionally, metal salts, such as calcium chloride, may be used to stabilize the compound. The hydrogel is pH stabilized, with triethanolamine (TEA) for example, to reduce degradation of the compound, if pH sensitive, and stabilize the final product. The hydrogel is allowed to cool to room temperature and the viscosity is controlled by the amount of polymer used.

Gels may be composed of viscous mixtures of water with glycerol that may be applied to the skin. They are typically soothing and particularly convenient to apply. The most commonly used bases are glycerol, propylene glycol, polyethylene glycol, and water. Water-based adhesive gels, or hydrogels, may be further used to increase viscosity. Hydrogels, such as those prepared with polyacrylic acids, povidones, celluloses, or aloe, are popular in a variety of topical preparations.

Osmotic pressure is primarily responsible for the direction and rate of movement of water across membranes in the body. The allocation of water between a wound, blood plasma, and cells depends upon the relative osmotic pressures between these sites. Besides electrolytes, glycerol and other compounds which may be used to improve wound remodeling and energy metabolism include glucose, pyruvate, alanine, and/or lactate, which are particularly useful because they function to enhance the energy available for cells (U.S. Pat. No. 5,238,684). The presence of pyruvate or lactate as secondary energy sources improves performance and helps to prevent the detrimental breaking down of protein as an energy source. The compounds added to the electrolyte/glucose solution or gel may be used as a simple gel or as an improved carrier for other agents.

The compositions of the present invention may be applied in any of a wide variety of topical application forms, including solutions such as a hydrogel, tinctures, creams, ointments, gels, lotions, and/or aerosol sprays. Such preparations may be either alcohol- or water-based or a combination of alcohol/water base.

Topical dermatologic treatments may be used as cleansing agents, absorbents, anti-infective agents, anti-inflammatory agents, emollients (skin softeners), and keratolytics (agents that soften, loosen, and facilitate exfoliation of the squamous cells of the epidermis). The base (vehicle or carrier) for a topical formulation may alter the effectiveness of the active ingredient and must be selected carefully.

Disclosed herein are compositions for topical application to the skin and/or a wound. In one non-limiting embodiment, the compositions include a suspension or dispersion of particles of at least one poorly soluble drug chelated or otherwise complexed with a physiologically acceptable salt, such as a calcium salt. The compositions further contain at least one physiologically acceptable carrier, and optionally further contain at least one stabilizer and/or at least one excipient.

One non-limiting embodiment of the present disclosure is a composition for topical application to the skin or a wound comprising: a suspension or dispersion of particles of at least one tetracycline class compound complexed with a physiologically acceptable metal salt, wherein the composition further comprises at least one stabilizer, at least one excipient, and at least one physiologically acceptable carrier, and said particles have an average diameter less than or equal to about 100 microns.

Another non-limiting embodiment of the present disclosure is a composition for topical application to skin or a wound, comprising a suspension or dispersion of particles of at least one tetracycline class compound chelated to a physiologically acceptable calcium salt, wherein the composition further includes a carboxy-methyl-cellulose hydrogel, glycerol, water, and at least one pH stabilizer, and said particles have an average diameter less than or equal to about 100 microns.

A further non-limiting embodiment of the present disclosure is a method of making a composition for topical application to skin and/or a wound, the method comprising mixing particles of at least one tetracycline class compound with at least one physiologically acceptable metal salt to form metal-chelated particles, said particles having an average diameter less than or equal to about 100 microns; combining said metal-chelated particles with at least one physiologically acceptable carrier to form a suspension or dispersion of metal-chelated particles, and optionally combining at least one excipient and/or at least one stabilizer with said suspension or dispersion.

Also disclosed herein are pharmaceutical formulations that include the compositions disclosed herein, methods for making such compositions, and methods of treatment utilizing such compositions.

Also disclosed herein are methods of treating skin or a wound, comprising, providing a pharmaceutical formulation comprising an effective amount of a composition of Doxycycline as described above, and topically administering said pharmaceutical formulation to skin or a wound on a patient in need thereof.

One aspect of the present disclosure relates to topical compositions for application to the skin and/or a wound. In general, the compositions disclosed herein include a suspension or dispersion of particles in a physiologically acceptable carrier, wherein the particles include at least one poorly soluble drug, such as a tetracycline class compound, that is chelated or otherwise complexed with a physiologically acceptable salt. The suspension/dispersion may also include at least one stabilizer and/or at least one excipient.

As used herein, the term, "drug" encompasses the free base form of a drug, as well as the corresponding salts, hydrates, solvates, prodrugs, chelates, and complexes of the drug. Thus, drugs in accordance with the present disclosure may be present, for example, in the form of a free base, a salt, a hydrate, a prodrug, a solvate (including a mixed solvate), a chelate (such as a pharmaceutically acceptable chelate with a metal salt), or a complex (such as a pharmaceutically acceptable complex, and/or a complex with a polymer).

As used herein, the term "complex" means a reversible association of compounds, molecules, atoms, etc. In contrast, the term "chelate" refers to a specific type of complex, namely a one in which a metal ion is attached to two or more bonds of the same molecule (ligands).

As used herein, the term, "poorly soluble drug," refers to a drug that, in its neutral (i.e., uncharged) state, has a relatively low solubility in water. For example, in some embodiments of the present disclosure, the poorly soluble drug is chosen from drugs having a solubility in the neutral state at neutral pH of about 10 mg/ml or less, such as about 5 mg/ml or less, or even about 1 mg/ml or less.

As used herein, the term "particulate delivery system" refers to particles of a poorly soluble drug, such as Doxycyline, in an aqueous hydrogel.

As examples of poorly soluble drugs that may be used in accordance with the present disclosure, non-limiting mention is made of tetracycline class compounds, such as Doxycycline, which has a solubility of less than 10 mg/ml at neutral pH.

In some embodiments of the present disclosure, the at least one poorly soluble drug is chosen from tetracycline antibiotics. Tetracycline antibiotics include, for example, naturally-occurring and semi-synthetic, e.g. Doxycycline, Chlortetracycline, Clomocycline, Demeclocycline, Lymecycline, Meclocycline, Metacycline, Minocycline, Oxytetracycline, Penimepicycline, Rolitetracycline, and Tetracycline.

The at least one poorly soluble drug may be present in any amount suitable for a desired application. For example, the at least one poorly soluble drug may be present in an amount ranging from less than about 1% to about 90 weight %, relative to the weight of the composition. Of course, a higher or lower concentration of the at least one poorly soluble drug may be used, and the concentration may vary within the aforementioned range. For example, the poorly soluble drug may be present in an amount ranging from about 0.01% to about 90%, about 0.01% to about 10%, about 0.2 to about 5%, about <1% to about 10%, about 0.01% to about 10%, about 0.1% to about 10%, about 0.01% to about 5%, about 0.1% to about 5%, about 0.1% to about 3%, less than about 1% to about 50%, less than about 1% to about 30%, less than about 1% to about 80%, about 5% to about 90%, about 10% to about 95%, or about 0.1 to about 5% by weight, relative to the weight of the composition. In some embodiments, the at least one poorly soluble drug is present in an amount ranging from about 0.3 to about 3% by weight (e.g., about 1% by weight) relative to the weight of the composition.

The particle size of the at least one poorly soluble drug may be controlled to any desired size, so long as the particles of at least one poorly soluble drug have an average particle diameter suitable for topical application to the skin and/or a wound. For example, the particles of at least one poorly soluble drug may have an average particle size less than about 1000 microns, e.g., less than about 500 microns, less than about 300 microns, less than about 150 microns, or less than about 100 microns Of course, particles of at least one poorly soluble drug having a larger or smaller average diameter may be used, and the average diameter may vary incrementally within the aforementioned range. In some embodiments, the particle size of the at least one poorly soluble drug ranges from about 1 to about 10 microns The at least one poorly soluble drug is chelated or otherwise complexed with at least one physiologically acceptable salt, e.g., a physiologically acceptable metal salt. As examples of physiologically acceptable metal salts which may be used in accordance with the present disclosure, non-limiting mention is made of calcium salts (e.g., calcium chloride) and zinc salts.

The physiologically acceptable carrier may impact the effectiveness of the at least one poorly soluble drug and should be selected with appropriate care to ensure that a desired effectiveness of the at least one poorly soluble drug is obtained. Thus, in some embodiments of the present disclosure, the physiologically acceptable carrier is chosen from polymers, such as water-soluble polymers, polymers of neutral charge, or water-soluble polymers of neutral charge. The physiologically acceptable carrier may also be considered by the FDA to be generally regarded as safe (GRAS). As examples of physiologically acceptable carriers which may be used in accordance with the present disclosure, non-limiting mention is made of hydrogels, including cellulose containing hydrogels such as carboxy-methyl-cellulose (CMC). In some embodiments of the present disclosure, the at least one physiologically acceptable carrier also includes at least one of water, glycerol, and mixtures thereof.

The average molecular weight of the physiologically acceptable carrier may range, for example, from about 100 Daltons (Da) to about 1,000,000 Da, such as from about 500,000 Da to about 1,000,000 Da.

The viscosity of the physiologically acceptable carrier may also be chosen to suit a desired application. For example, the viscosity of the physiologically acceptable carrier may range from greater than 0 to about 10,000 centipoise (cps) or more, such as from about 100 to about 10,000 cps, from about 500 to about 5,000 cps, or even from about 1000 to about 3000 cps. In some embodiments, the physiologically acceptable carrier is a high viscosity CMC that exhibits a viscosity ranging from about 1,500 to about 3,000 cps, as measured from a 1% solution of CMC in water at 25 degrees Celsius. In many instances, the viscosity of the physiologically acceptable carrier is both concentration and temperature dependent. That is, the viscosity may decrease as temperature increases, and vice versa. Similarly, the viscosity may decrease as concentration decreases, and vice versa.

In some embodiments, the compositions of the present disclosure also include at least one stabilizer. Such stabilizers may serve a variety of purposes. For example, stabilizers may be added to the compositions of the present disclosure for the purpose of buffering the pH and/or the viscosity of the physiologically acceptable carrier (e.g., a hydrogel) in the presence of various metal salts. The stabilizer may be natural or synthetic and is optionally biodegradable and/or bioerodable. Non-limiting examples of pH stabilizers that are suitable for use in accordance with the present disclosure include buffering salts and organic chemical compounds such as triethanolamine, often abbreviated as TEA, which is both a tertiary amine and a tri-alcohol. Citric acid is also suitable for use in the present disclosure as a pH stabilizer.

The compositions of the present disclosure may also include at least one excipient. The at least one excipient may be chosen, for example, from surfactants (cationic, anionic, or neutral), surface stabilizers, and other enhancers, such as preservatives. Non-limiting examples of surfactants that may be used in accordance with the present disclosure include nonionic surfactants such as a polysorbate surfactant (e.g., polysorbate 20 (Tween 20™), and polysorbate 80 (Tween 80™)). In some embodiments, the compositions of the present disclosure contain multiple pH stabilizers so as to form a pH buffering system within the composition. As an example of a preservative that may be added to the compositions of the present disclosure, non-limiting mention is made of glycerol, which may act as a preservative at certain concentrations.

The compositions of the present disclosure may also include at least one emulsifier. Non-limiting examples of suitable emulsifiers include, phospholipids, propylene glycol, polysorbate, poloxamer, and glyceryl monostearate. Of course, other known pharmaceutical emulsifiers may be used.

The compositions of the present disclosure may be in any form suitable for topical application to the skin and/or a wound. The compositions of the present disclosure may be in the form of a topical dermatologic treatment. For example, the compositions disclosed herein may be in the form of a cleansing agent, an absorbent, an anti-infective agent, an anti-inflammatory agent, an emollient (skin softener), and a keratolytic (i.e., an agent that softens, loosens, and facilitates exfoliation of the squamous cells of the epidermis).

The present disclosure also relates to methods for manufacturing compositions in accordance with the present disclosure. In some embodiments, a composition in accordance with the present disclosure is prepared by heating or autoclaving a physiologically acceptable carrier (e.g., a hydrogel), and then combining doxycycline with the physiologically acceptable carrier at 70 degrees Celsius or less while mixing. After the components are mixed, the final product is allowed to cool to room temperature. The viscosity of the final product may be controlled, for example, by controlling the amount of stabilizer and/or other components.

Methods of preparing the disclosed preparation may include the formation of the suspension/dispersion under high shear conditions. In addition, the suspension/dispersion may be formed using low-frequency sonication (LFS), e.g., at a frequency ranging from about 1 to about 1,000 hertz, as described in U.S. Pat. Appl. Pub. No. 2005/0175707, which is incorporated herein by reference. The use of LFS may result in improved homogeneity of the composition, relative to conventional propeller mixers or homogenizers. In addition, the size of the particles may be controlled by the intensity of the LFS as well as by controlling other conditions during the formation of the suspension/dispersion.

The composition of the present disclosure may also be present in a system for delivering an effective amount of at least one poorly soluble drug, such as a particle delivery system ("PDS"). For example, in one non-limiting embodiment, PDS includes particles of at least one poorly soluble drug, such as Doxycycline, chelated to a physiologically acceptable metal salt and dispersed and/or suspended within at least one physiologically acceptable carrier. In some embodiments, the particles of the at least one poorly soluble drug are fine particles with an average diameter of less than about 100 microns, such as about 1 to about 10 microns In another non-limiting embodiment, a composition or PDS in accordance with the present disclosure includes at least one hydrogel composed of at least one physiologically acceptable carrier and a solvent. As examples of suitable physiologically acceptable carriers, non-limiting mention is made of glycerol, propylene glycol, polyethylene glycol. A non-limiting example of a suitable solvent is water. Of course, other physiologically acceptable carriers and solvents may be used.

In some embodiments, the compositions and/or PDS of the present disclosure include at least one water-based hydrogel. As non-limiting examples of such hydrogels, mention is made of hydrogels prepared from polyacrylic acids, povidones, celluloses, and aloe. In some embodiments, a carboxy-methyl-cellulose hydrogel is used. Of course, other hydrogels may also be used in accordance with the present disclosure.

Another aspect of the present disclosure relates to pharmaceutical formulations comprising at least one composition described herein, and/or at least one PDS comprising at least one composition described herein.

In some embodiments, the pharmaceutical formulations further comprise at least one excipient, such as a water-soluble polymer, a surfactant, and/or another enhancer such as a pharmaceutically acceptable excipient. Non-limiting examples of pharmaceutically acceptable excipients are described in Remington's Pharmaceutical Sciences by E. W. Martin, and include cellulose, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In some embodiments, the pharmaceutical formulations also contain pH buffering reagents, and wetting or emulsifying agents.

The pharmaceutical formulations of the present disclosure can be in the any form suitable for administration to a patient, such as in the form of an aqueous dispersion or suspension. The pharmaceutical formulations may also contain various additional ingredients, such as suspending, stabilizing and/or dispersing agents.

In some embodiments, the pharmaceutical formulations described herein provide improved local concentrations of the poorly soluble drug, relative to the unformulated poorly soluble drug. For example, the local concentration may be increased by, e.g., at least 10%, 15%, 20%, 25%, 30%, 35%, 40%, 50%, 60%, 70%, 80%, 90%, 93%, 95%, 96%, 97%, 98%, 99%, 100%, 110%, 120%, 130%, 140%, 150%, or 200%, or by, e.g., at least 2, 3, 4, 5, 6, 7, 8, 9, 10, 20, 30, 40, 50, 100, or 1000 fold, as measured by, e.g., in vivo tissue distribution studies in a preclinical animal model or human clinical evaluation.

In some embodiments, the pharmaceutical formulations are in the form of a controlled-release formulation.

In some embodiments, the pharmaceutical formulations described herein are associated with improved patient compliance, relative to another pharmaceutical formulation comprising the same poorly soluble drug (which may be in another dosage form, e.g., a more invasive dosage form such as an injectable product).

Another aspect of the present disclosure relates to methods of treatment that include the topical administration of at least one composition and/or particulate delivery system in accordance with the present disclosure to the skin and/or a wound of a patient in need thereof.

As used herein, the terms "treat," "treatment," and "treating" refer to (1) a reduction in severity or duration of a disease or condition, (2) the amelioration of one or more symptoms associated with a disease or condition without necessarily curing the disease or condition, or (3) the prevention of a disease or condition. Suitable subjects include, e.g., humans and other mammals, such as, e.g., mice, rats, dogs, and non-human primates.

In some embodiments, for example, the method includes the topical application of a composition containing an effective amount of at least one poorly soluble drug chelated to a physiologically acceptable salt (e.g., a physiologically acceptable metal salt) and dispersed and/or suspended in at least one physiologically acceptable carrier. In some instances, such a method results in beneficial (i.e., improved) wound healing, rate of wound closure, reduced inflammation, and/or reduced rate/amelioration of infection.

In some embodiments, the methods of treatment include applying a composition comprising a suspension/dispersion comprising at least one physiologically acceptable carrier (e.g., water), glycerol, wherein the suspension/dispersion comprises a physiologically acceptable carrier (e.g., a natural or synthetic polymer such as carboxy-methyl-cellulose), and at least one tetracycline antibiotic such as Doxycycline chelated to a physiologically acceptable salt, such as a calcium salt (e.g., calcium chloride). In such methods, the at least one poorly soluble drug may, for example be, present in an amount greater than about 0.1 weight % relative to the mass of the composition, such as from about 0.3% to about 1.0% by mass, or more. In some embodiments, the at least one poorly soluble drug includes Doxycycline chelated to at least one physiologically acceptable calcium salt as a fine particle suspension of particles having an average diameter less than about 100 microns (e.g., from about 1 to about 10 microns), as measured by optical microscopy.

The following examples are intended to be purely exemplary of the present invention.

EXAMPLES

Example 1—Preparation of Doxycycline Monohydrate Hydrogel above 90 degrees Celsius. Two batches of doxycycline monohydrate hydrogel containing 0.3 (Lot #061708-03-01 prepared Jun. 17, 2008) and 1.0 (Lot #070908-10-01 prepared Jul. 9, 2008) weight % of USP grade Doxycycline Monohydrate (Spectrum Chemicals, Brunswick, N.J.) with carboxy-methyl-cellulose (CMC) hydrogel, calcium chloride, glycerol, water for injection (WFI), triethanolamine, and citric acid were prepared. Briefly, a 3% CMC solution was made for each batch by mixing USP grade CMC with WFI followed by autoclaving to dissolve fully the CMC into solution, resulting in the formation of a CMC hydrogel. A doxycycline suspension was made by adding doxycycline monohydrate (sieved to less than 150 micron particle size) to WFI into the CMC hydrogel after autoclaving at 90 to 96 degrees Celsius. Calcium chloride and stabilizers (TEA, citric acid) were added to the CMC hydrogel, whereby calcium was available to chelate the Doxycycline. The resulting combination was mixed under high shear conditions (paddle mixer) as the hydrogel cooled to 40 to 50 degrees Celsius. Glycerol and additional WFI were also added to the suspension to achieve a desired doxycycline concentration.

At this dilution and temperature, the Doxycycline chelated to calcium to form a stable, small particle suspension. The bulk hydrogel suspension was observed under an optical microscope at 100 to 200 times magnification. The primary particle size of the suspended particles was less than about 50 micrometers. The bulk hydrogel suspension was transferred to storage vessels (e.g., carboys), labeled, and placed into the refrigerator until packet filling was performed. The final product was packaged into medical grade foil-on-foil packets with 1.5 to 2.5 gram bulk hydrogel and then subjected to irradiation at a nominal 5 kGy. Stability testing for lots 061708-03-01 and 070908-10-01 under storage conditions of 5° C. for 12 months was conducted for appearance, assay and purity, and content. Table 1 shows the lot information and 12-month data for color, % active and impurity concentrations.

TABLE 1

| Lot # | % Doxy. | Process Temp. | Timepoint | Color | % Active | % 4-epidox. | % 6-epidox. |
|---|---|---|---|---|---|---|---|
| 061708-03-01 | 0.3 | 94° C. | 0 | Yellow | 104.5 | 0.25 | 0.59 |
| | | | 3 month | Yellow-Brown | 97.2 | 0.39 | 0.61 |
| | | | 6 month | Yellow-Brown | 97.3 | 0.47 | 0.51 |
| | | | 12 month | Brown | 84.6 | 0.52 | 0.63 |
| 070908-10-01 | 1.0 | 96° C. | 0 | Yellow-Brown | 100 | 0.21 | 0.59 |
| | | | 3 month | Yellow-Brown | 98.4 | 0.44 | 0.56 |
| | | | 6 month | Yellow-Brown | 97.1 | 0.43 | 0.51 |
| | | | 12 month | Brown | 90.4 | 0.57 | 0.45 |

Both lots manufactured at 94-96 degrees Celsius process temperatures failed the assay and appearance specifications for the 12 month time point at 5° C. storage temperature. At 12 months at 5 degrees Celsius lot 061708-03-01 had a mean value of 84.6% active (degradation rate=19.3%/year) and 070908-10-01 had a mean value of 90.4% active (degradation rate 8.72%/year) with four of the samples below 90% of the label claim. The related substances specifications for doxycycline monohydrate are outlined in the USP 32 NF 27. The doxycycline monograph states the following specifications for related substances: not more than 2% of methacycline; not more than 0.5% of any impurity eluting before methacycline (includes 4-epidoxycycline); not more than 2% of 6-epidoxycycline; and not more than 0.5% of any impurity eluting after the main doxycycline peak is found. Three impurity peaks above 0.5% were observed for 070908-10-01 throughout the twelve-month stability study stored at 5° C. Four impurity peaks above 0.5% were observed for 061708-03-01 stored at 5° C.

Example 2—Preparation of Doxycycline Monohydrate Hydrogel at 90 degrees Celsius

An additional batch of doxycycline monohydrate hydrogel (Lot #100711-10-01-2 prepared Oct. 7, 2011) containing 1.0 weight % of USP grade Doxycycline Monohydrate (Spectrum Chemicals, Brunswick, N.J.) with CMC hydrogel, calcium chloride, glycerol, WFI, triethanolamine, and citric acid was prepared in a similar fashion to Example 1. The doxycycline suspension was added into the CMC hydrogel at 90 degrees Celsius. The bulk hydrogel suspension was transferred to storage vessels (e.g., carboys), labeled, and placed into the refrigerator until packet filling was performed. The final product was packaged into medical grade foil-on-foil packets with 1.5 to 2.5 gram bulk hydrogel and then subjected to irradiation at a nominal 5 kGy. Stability testing under storage conditions of 5° C. and 25° C. for 12 months was conducted for appearance, assay and purity, and content. Table 2 shows the lot information and 12-month data for color, % active and impurity concentrations.

TABLE 2

| Lot # | % Doxy. | Storage Temp. | Timepoint | Color | % Active | % 4-epidox. | % 6-epidox. |
|---|---|---|---|---|---|---|---|
| 100711-10-01-2 | 1.0 | 5° C. | 0 | Yellow-Brown | 94.0 | 0.24 | 0.65 |
| | | | 3 month | Yellow-Brown | 93.0 | 0.35 | 0.61 |
| | | | 6 month | Yellow-Brown | 94.0 | 0.32 | 0.58 |
| | | | 9 month | Yellow-Brown | 90.0 | 0.37 | 0.57 |
| | | | 12 month | Yellow-Brown | 86.0 | 0.41 | 0.58 |
| 100711-10-01-2 | 1.0 | 25° C. | 0 | Yellow-Brown | 94.0 | 0.24 | 0.65 |
| | | | 1 month | Yellow-Brown | 92.0 | 0.47 | 0.59 |
| | | | 3 month | Brown | 83.0 | 1.09 | 0.47 |
| | | | 6 month | Brown | 87.0 | 1.7 | 0.49 |

The lot manufactured at 90 degrees Celsius process temperature failed the assay and appearance specifications for the 12 month time point at 5° C. storage temperature and the 3 month time point at 25° C. storage temperature (room temperature). At 12 months at 5 degrees Celsius lot 100711-10-01-2 had a mean value of 86% active (degradation rate=8%/year) and at 6 months at 25 degrees Celsius had a mean value of 87% active (degradation rate 20.1%/year), both sets below 90% of the label claim.

Example 3—Preparation of Doxycycline Monohydrate Hydrogel batches at 70 to 76 degrees Celsius. Three additional batches of doxycycline monohydrate hydrogel (Lots #ND1703007 prepared Mar. 22, 2017, #ND1703008 prepared Apr. 18, 2017 and #ND1708001 prepared Aug. 8, 2017) containing 1.0 weight % of USP grade Doxycycline Monohydrate (Spectrum Chemicals, Brunswick, N.J.) with CMC hydrogel, calcium chloride, glycerol, WFI, triethanolamine, and citric acid was prepared in a similar fashion to Example 1. The doxycycline suspension was added into the CMC hydrogel at 70 (Lots #ND1703007 and #ND1708001) and 76 (Lot #ND1703008) degrees Celsius. The bulk hydrogel suspension was transferred to storage vessels (e.g., carboys), labeled, and placed into the refrigerator until packet filling was performed. The final product was packaged into medical grade foil-on-foil packets with 1.5 bulk hydrogel and then subjected to irradiation at a nominal 5 kGy. Stability testing under storage conditions of 5° C. for 12 months was conducted for appearance, assay and purity, and content. Table 3 shows the lot information and 20-month data for color, % active and impurity concentrations.

TABLE 3

| Lot # | % Doxy. | Process Temp. | Timepoint | Color | % Active | % 4-epidox. | % 6-epidox. |
|---|---|---|---|---|---|---|---|
| ND1703007 | 1.0 | 70° C. | 0 | Yellow | 103.0 | 0.25 | 0.6 |
| | | | 9 month | Yellow-Brown | 100.0 | 0.45 | 0.55 |
| | | | 12 month | Yellow-Brown | 102.0 | 0.21 | 0.54 |
| | | | 14 month | Yellow-Brown | 102.0 | 0.26 | 0.46 |
| | | | 20 month | Yellow-Brown | 104.0 | 0.17 | 0.37 |
| ND1703008 | 1.0 | 76° C. | 0 | Yellow | 99.0 | 0.32 | 0.68 |
| | | | 9 month | Yellow-Brown | 101.0 | 0.42 | 0.6 |
| | | | 12 month | Yellow-Brown | 105.0 | 0.45 | 0.66 |
| | | | 14 month | Brown | 89.0 | 0.51 | 0.72 |
| ND1708001 | 1.0 | 70° C. | 0 | Yellow | 107.0 | 0.3 | 0.6 |
| | | | 9 month | Yellow-Brown | 99.0 | 0.31 | 0.69 |
| | | | 12 month | Yellow-Brown | 108.0 | 0.35 | 0.61 |
| | | | 14 month | Yellow-Brown | 102.0 | 0.34 | 0.64 |
| | | | 20 month | Yellow-Brown | 97.0 | 0.36 | 0.69 |

Lot #ND1703008 manufactured at 76 degrees Celsius process temperature had a mean value of 89% active (degradation rate=8%/year) passed the assay and appearance specifications for the 12 month time point but failed the assay and appearance specifications at the 14 month time point at 5° C. storage temperature. Lot #ND1703008 4-epidoxycycline concentrations remained below 0.5% from 0 to 12 months and increased to 0.51% at 14 months correlating to failure of the 90% assay specification and the transition to brown color. Lots #ND1703007 and #ND1708001 manufactured at 70 degrees Celsius process temperatures passed the assay and appearance specifications for the 12 and 20 month time point at 5° C. storage temperature. At 20 months at 5 degrees Celsius lot #ND1703007 had a mean value of 104% active (degradation rate=0.7%/year) and #ND1708001 had a mean value of 97% active (degradation rate 5%/year). Lots #ND1703007 and #ND1708001, manufactured at 70 degrees Celsius process temperatures, demonstrated 4-epidoxycycline concentrations below 0.5% up to 20 months passing according to the 90% assay specification and remained yellow-brown in color.

Example 4—Preparation of Doxycycline Monohydrate Hydrogel batches at 50 degrees Celsius. One additional batch of doxycycline monohydrate hydrogel (Lots #ND1806001 prepared Jun. 5, 2018) containing 1.0 weight % of USP grade Doxycycline Monohydrate (Spectrum Chemicals, Brunswick, N.J.) with CMC hydrogel, calcium chloride, glycerol, WFI, triethanolamine, and citric acid was prepared in a similar fashion to Example 1. The doxycycline suspension was added into the CMC hydrogel at 50 degrees Celsius. The bulk hydrogel suspension was transferred to storage vessels (e.g., carboys), labeled, and placed into the refrigerator until packet filling was performed. The final product was packaged into 90 mL Amber Topi-Pump Tubes with 1.0 mL dispenser tops (Topi-Pump, TCD Inc.) in a Class 100 hood without terminal sterilization. Stability testing under storage conditions of 5° C. for 6 months was conducted for appearance, assay and purity, and content.

Table 4 shows the lot information and 6-month data for color, % active and impurity concentrations.

TABLE 4

| Lot # | % Doxy. | Process Temp. | Timepoint | Color | % Active | % 4-epidox. | % 6-epidox. |
|---|---|---|---|---|---|---|---|
| ND1806001 | 1.0 | 50° C. | 0 | Yellow | 101 | 0 | |
| | | | 1 month | Yellow | 101 | 0.29 | 0.72 |
| | | | 4 month | Yellow | 98 | 0.24 | 0.51 |
| | | | 6 month | Yellow-Brown | 96 | 0.26 | 0.68 |

Lot #ND1806001 manufactured at 50 degrees Celsius process temperature had a mean value of 96% active (degradation rate=5%/year) passed the assay and appearance specifications for the 6 month time point at 5° C. storage temperature. 4-epidoxycycline concentration remained below 0.5% from 0 to 6 months and remained yellow-brown in color.

Example 5—Determination of Assay, Related Substances, and Identification of Doxycycline in 1% Doxycycline Monohydrate Hydrogel and Absence of Active in Placebo Gel, by HPLC. Analytical data that demonstrates the stability of doxycycline in standard/sample solutions was obtained using HPLC according to the USP method. The known related substance solutions of Oxytetracycline (Impurity E), Methacycline Hydrochloride (Impurity B), Doxycycline Related Compound A (Impurity A, 6-epidoxycycline), Doxycycline Related Compound C (Impurity C, 4-epidoxycycline), Doxycycline Related Compound D (Impurity D, 4-epi-6-epidoxycycline), and API Doxycycline Monohydrate were prepared individually. No peaks greater than 1% were observed in the placebo selectivity sample. Samples of 1% Doxycycline Monohydrate Hydrogel and control sample blanks were evaluated under stressed conditions using light, heat, acid, base and oxidation. Freshly prepared sample solutions were used for acid, base and oxidation stress studies over 24+ hours. A non-stressed control sample and a blank for each stress condition were evaluated as controls. The percent degradation (area/area %) was calculated by comparing the stressed sample against that of the control.

TABLE 5

| Treatment | Treatment Condition | % Purity (a/a %) | Total Impurities (a/a %) | Impurity C (4-epidox.) | Impurity D (4-epi-6-epidoxycycline) | Impurity A (6-epidox.) |
|---|---|---|---|---|---|---|
| Unstressed Sample | — | 98.03 | 1.97 | 0.51 | 0.70 | — |
| Heat (60° C.) | 60° C. | 85.97 | 14.03 | 10.30 | 0.87 | 0.59 |
| Light (UV & White) | UV & White | 66.11 | 33.89 | 4.68 | 4.95 | — |
| Oxidation (0.3% $H_2O_2$) | 0.3% $H_2O_2$ | 97.87 | 2.12 | 0.44 | 0.06 | 0.64 |
| Acid (0.1N HCl) | 0.1N HCl | 97.89 | 2.11 | 0.71 | — | 0.67 |
| Base (0.1N KOH) | 0.1N KOH | 94.06 | 5.91 | 0.34 | 0.85 | 0.74 |

The stressed solutions demonstrate significant degradation to light and heat degrading primarily to 4-epidoxycyline and 4-epi-6-epidoxycycline. Impurity C (4-epidoxycycline) was present in every sample. Impurity D (4-epi-6-epidoxycycline) was present in all 1% Doxycycline Monohydrate Hydrogel batches. Impurity E (Oxytetracycline) was not detected during the stability studies and only occurred under heat and base stress conditions. Impurity A (6-epidoxycycline) was present in every sample except the light stress sample. Impurity B (Methacycline Hydrochloride) was only detected in standard solutions.

Example 6—A Pilot Clinical Study to Investigate Safety and Efficacy of Doxycycline Monohydrate Hydrogel 1% In Atopic Dermatitis. Atopic Dermatitis (AD) is characterized by skin barrier disruption & an aberrant immune response (e.g. Th2 polarized) to environmental allergens. Pruritus and cutaneous infections are major drivers of the reduced quality-of-life associated with this disease. Oral doxycycline is broadly used to treat inflammatory-dermatologic conditions. Several studies in human and animal models have shown that doxycycline has anti-inflammatory and pro-healing properties, mainly by blocking tissue proteolytic activity. The aim of this pilot clinical study (n=15 patients) was to investigate the safety and clinical efficacy of 1% topical Doxycycline Monohydrate hydrogel in AD. Our hypothesis was that daily application of 1% topical Doxycycline Monohydrate hydrogel blocking cutaneous proteases activity in AD subjects will reduce severity of the disease by restoring skin barrier function and reducing skin driven inflammation. Eligible patients with AD (n=15) were dosed topically for 4 weeks by daily application of 1% Doxycycline Monohydrate hydrogel (Lots #ND1703007, #ND1703007 and #ND1708001 passing assay and appearance specifications) to the irritated skin area. Clinical improvement was assessed using the Investigator Global Assessment (IGA, 0-4) and Eczema Area & Severity Index (EAST) score before and after 4 weeks treatment.

Significant clinical improvement was observed after 4 weeks of treatment with 1% topical Doxycycline Monohydrate hydrogel demonstrating a beneficial safety profile and clinical efficacy. No local or systemic Adverse Event (AE) or Severe AE's were observed during the trial due to daily application of 1% topical Doxycycline Monohydrate hydrogel. Investigational drug was well tolerated with mild yellow discoloration observed in one (1/15) subject. Improvement of EASI (4.53, p<0.001) and IGA (16.57, p<0.001) scores from initiation to week 4 was significant. These results provide evidence of 1% topical Doxycycline Monohydrate hydrogel as a novel AD treatment targeting cutaneous proteases activity.

Additional objects and advantages of the present disclosure will be apparent from the description or may be learned by practice of the present disclosure. The objects and advantages of the present disclosure will be realized and attained by means of the elements and combinations particularly pointed out in the specification and the appended claims. It is to be understood that the foregoing general description is exemplary and explanatory only and is not limiting of the invention as claimed.

Other embodiments of the invention will be apparent to those skilled in the art from consideration of the specification and practice of the invention disclosed herein. It is intended that the specification and examples be considered as exemplary only, with the true scope and spirit of the invention being indicated by the claims that follow.

It will be recognized by those skilled in the art that changes may be made to the above-described embodiments of the invention without departing from the broad inventive concepts hereof. The present invention is not limited to the particular embodiments disclosed herein, but it is intended to cover all modifications which are within the scope and spirit of the invention as defined by the appended claims.

The invention claimed is:

1. An aqueous hydrogel composition for topical applications to skin or a wound, comprising:
   doxycycline with carboxy-methyl-cellulose (CMC), glycerol, citric acid, and at least one pH stabilizer, wherein the doxycycline is added in an autoclaved CMC hydrogel after cooling to a temperature of 50 to 70 degrees Celsius; and
   a suspension or dispersion of particles of doxycycline chelated with calcium, the particles having an average diameter less than or equal to about 100 microns,
   wherein the doxycycline chelated with calcium is present in an amount ranging from greater than about 0.1 weight % to about 3 weight %,
   wherein the composition includes less than 0.5 weight % 4-epidoxycycline,
   wherein the formation of 4-epidoxycycline is less than 0.5 weight % per year under refrigeration,
   wherein storage of the composition for greater than one year under refrigeration, or exposure to higher temperatures, results in the formation of 4-epidoxycycline in amounts greater than 0.5 weight %,
   wherein the composition is a yellow color when the composition contains an amount of 4-epidoxycycline less than 0.5 weight %,
   wherein the composition is a brown color when the composition contains an amount of 4-epidoxycycline greater than 0.5 weight %, and
   wherein the topical applications include skin and/or a wound.

* * * * *